(12) United States Patent
Petito

(10) Patent No.: US 9,125,892 B2
(45) Date of Patent: Sep. 8, 2015

(54) COMPOSITION FOR REDUCED SCAR FORMATION OF WOUNDS

(71) Applicant: George D. Petito, Bethlehem, PA (US)

(72) Inventor: George D. Petito, Bethlehem, PA (US)

(*) Notice: Subject to any disclaimer, the term of this patent is extended or adjusted under 35 U.S.C. 154(b) by 0 days.

(21) Appl. No.: 14/547,120

(22) Filed: Nov. 18, 2014

(65) Prior Publication Data

US 2015/0216946 A1  Aug. 6, 2015

Related U.S. Application Data

(60) Provisional application No. 61/935,098, filed on Feb. 3, 2014.

(51) Int. Cl.
| | |
|---|---|
| *A61K 8/02* | (2006.01) |
| *A61K 38/39* | (2006.01) |
| *A61K 33/30* | (2006.01) |
| *A61K 45/06* | (2006.01) |
| *A61K 31/385* | (2006.01) |
| *A61K 31/7008* | (2006.01) |

(52) U.S. Cl.
CPC .............. *A61K 38/39* (2013.01); *A61K 31/385* (2013.01); *A61K 31/7008* (2013.01); *A61K 33/30* (2013.01); *A61K 45/06* (2013.01)

(58) Field of Classification Search
CPC ....... A61K 38/39; A61K 33/30; A61K 45/06; A61K 31/385; A61K 31/7008
See application file for complete search history.

(56) References Cited

U.S. PATENT DOCUMENTS

| | | |
|---|---|---|
| 6,136,341 A | 10/2000 | Petito |
| 7,939,570 B2 | 5/2011 | Raul et al. |
| 8,168,599 B2 | 5/2012 | Petito et al. |
| 8,389,021 B2 | 3/2013 | Baker |
| 8,563,045 B2 | 10/2013 | Ishaq |
| 2007/0190004 A1* | 8/2007 | Bockmuhl et al. .............. 424/65 |
| 2008/0154210 A1* | 6/2008 | Jordan et al. .................. 604/210 |
| 2010/0092577 A1* | 4/2010 | Guasti ........................... 424/618 |
| 2010/0310654 A1 | 12/2010 | Jacono |
| 2013/0108700 A1 | 5/2013 | Nguyen et al. |

OTHER PUBLICATIONS

Weller, Carolina et al., "Wound Dressings Update," *Journal of Pharmacy Practice and Research*, vol. 36, No. 4, 318-324, 2006.

\* cited by examiner

*Primary Examiner* — Lezah Roberts
*Assistant Examiner* — Nannette Holloman
(74) *Attorney, Agent, or Firm* — Richard C. Litman

(57) ABSTRACT

A composition for reduced scar formation of wounds includes hydrolyzed collagen and one or more supplemental ingredients, including, lipoic acid, a zinc component, and a glucosamine component. The composition may facilitate inhibition of scar formation during wound healing. The composition may be used, for example, as a topical dressing for a wound, including, an acute or chronic wound.

2 Claims, No Drawings

COMPOSITION FOR REDUCED SCAR FORMATION OF WOUNDS

CROSS-REFERENCE TO RELATED APPLICATION

This application claims the benefit of U.S. Provisional Patent Application Ser. No. 61/935,098, filed Feb. 3, 2014.

BACKGROUND OF THE INVENTION

1. Field of the Invention

The present invention relates to a composition for inhibiting the formation of scars associated with wounds. The invention particularly pertains to a composition for inhibiting scar formation comprising hydrolyzed collagen as the basic ingredient.

2. Description of the Related Art

Scarring is a natural response to the healing of wounds in a patient's skin. The wound healing process can be divided into three successive stages. A first inflammatory stage begins immediately after the injury which caused the wound. The inflammatory stage lasts up to a week during which time cellular processes remove damaged tissue and foreign matter from the wound. The inflammatory stage is followed by a proliferative stage which is characterized by fibroblast proliferation and the production of collagen and proteoglycans. The proliferative stage can last from days to weeks and is typically the stage during which scar formation begins. After the proliferative stage, a remodeling phase begins where the matrix which was produced in the proliferative stage is remodeled into an organized, cross-linked structure which increases the mechanical strength of the healed tissue.

Scars which are formed during the healing response are often treated after the healing is complete by cosmetics or surgical treatment. Cosmetic treatments are at best temporary solutions, and the need to have subsequent surgery is both inconvenient and a risk to the patient. It would therefore be desirable to provide a composition which could diminish scar formation during the healing process itself so that such subsequent procedures would be unnecessary or at least reduced in scope.

Thus, a composition useful for scar reduction during wound healing is desired.

SUMMARY OF THE INVENTION

A composition for reduced scar formation of wounds may include hydrolyzed collagen and one or more supplemental ingredients, including, lipoic acid; a zinc component, and a glucosamine component. The composition may facilitate inhibition of scar formation during wound healing. The composition may be used, for example, as a topical dressing for a wound, including, an acute or chronic wound.

These and other features of the present invention will become readily apparent upon further review of the following specification.

DETAILED DESCRIPTION OF THE PREFERRED EMBODIMENTS

The present composition may facilitate a reduction in scar formation during wound healing. The present composition may include hydrolyzed collagen and one or more zinc components, one or more glucosamine components, and/or lipoic acid. For example, the composition may include hydrolyzed collagen and lipoic acid. The composition may include hydrolyzed collagen, lipoic acid, and one or more zinc components. The composition may include hydrolyzed collagen, lipoic acid, and one or more glucosamine components. The composition may include hydrolyzed collagen, lipoic acid, one or more zinc components, and one or more glucosamine components. The composition may include hydrolyzed collagen, one or more zinc components and/or one or more glucosamine components. The composition may be used as a topical dressing for any type of wound, including, e.g., acute or chronic wounds. The composition may be applied to the wound at any time during the healing stage of the wound, and preferably before scar formation begins.

Hydrolyzed collagen is a collagen hydrolysate polypeptide. Hydrolyzed collagen may be obtained by hydrolysis of native collagen. This may be accomplished by one of four methods: (1) alkaline hydrolysis; (2) enzymatic hydrolysis; (3) acid hydrolysis; and (4) synthetically by fermentation. Any of these methods can be used to derive the hydrolyzed collagen from either a bovine (skin and tendon preferred), porcine, fish, avian or a synthetic source. The types of amino acid constituents and their sequences determine the beneficial healing qualities of hydrolyzed collagen. Hydroxylysine and hydroxyproline are amino acids found only in collagen and in no other medical protein hydrolysates. Hydroxylysine is typically found in concentrations from 0.7 to 1.2 wt. % in hydrolyzed collagen.

The hydrolyzed collagen of the present composition may have a molecular weight of from about 500 Daltons to about 150,000 Daltons. For example, the hydrolyzed collagen may have a molecular weight of from about 500 Daltons to about 10,000 Daltons. The hydrolyzed collagen may have a molecular weight above 10,000 Daltons. For example, the hydrolyzed collagen may have a molecular weight between 10,000 Daltons and 150,000 Daltons, e.g. between 10,000 Daltons and 100,000 Daltons. The hydrolyzed collagen may have a molecular weight of from about 100,000 Daltons to about 150,000 Daltons.

The composition may include hydrolyzed collagen and one or more zinc components, one or more glucosamine components, and/or lipoic acid. One or more zinc components may include, for example, zinc or a zinc salt. Zinc may help to prevent scarring by, for example, promoting tissue repair and alleviating inflammation associated with a wound. Zinc salts suitable for the present composition may include, for example, zinc gluconate and zinc acetate. One or more glucosamine components may be included in the composition in addition to or instead of the zinc components. These include glucosamine and/or any suitable form of glucosamine, for example, glucosamine hydrochloride and/or glucosamine sulfate. Glucosamine is a prominent precursor in the biochemical synthesis of glycosylated proteins and lipids. Glucosamine itself may be helpful for inhibiting scar formation. In addition, glucosamine is important for production of hyaluronic acid, which may also be useful for inhibiting scar formation. Another component which may be present in the composition is lipoic acid (LA), also known as α-lipoic acid and alpha lipoic acid (ALA). Lipoic acid may be present in the composition in addition to or instead of the zinc components and the glucosamine components. Lipoic acid is an organosulfur compound derived from octanoic acid. Lipoic acid may also reduce or eliminate the appearance of some forms of scarring by, for example, preventing activation of pro-inflammatory chemicals.

In addition to the ingredients described above, one or more additional therapeutic agents may be included in the composition to decrease scarring and increase tissue strength. Examples of suitable therapeutic agents which may be combined with the hydrolyzed collagen are glycosaminoglycans (GAGs), antimicrobials, and antibiotics, such as tetracycline, streptomycin, cephalosporin, and antibacterials, such as iodine, parachlorometaxylenol, and chlorhexidine gluconate or acetate.

Glycosaminoglycans (GAGs) are polysaccharides found in vertebrate and invertebrate animals. Several GAGs have been found in tissues and fluids of vertebrate animals. The known GAGs are chondroitin sulfate, keratin sulfate, dermatic sulfate, hyaluronic acid, heparin, and heparin sulfate. GAGs and collagen are the major structural elements of all animal tissue. Their synthesis is essential for proper repair, treatment, protection, and maintenance of all tissues. The composition may include, for example, hyaluronic acid and/or the sodium salt, sodium hyaluronate.

The hydrolyzed collagen may facilitate an injured tissue to repair itself by producing and remodeling more collagen and other proteoglycans (PGs). The building blocks for collagen production are the amino acids found in hydrolyzed collagen. The hyaluronic acid and other proteoglycans (PGs) may provide the framework for collagen production to follow. The PGs hold water to provide an excellent environment for healing of the tissue.

The present composition may include about 1% by weight to about 99% by weight hydrolyzed collagen. For example, the composition may include about 10% by weight to about 85% by weight hydrolyzed collagen or about 20% by weight to about 75% by weight hydrolyzed collagen or about 30% by weight to about 65% by weight hydrolyzed collagen. Other amounts below and above these ranges may be used.

The zinc components, glucosamine components, and lipoic acid components may be present in the composition alone or in combination, in an amount of from about 0.1% by weight to about 50% by weight or from about 20% by weight to about 50% by weight or from about 25% by weight to about 35% by weight of the total composition. For example, a zinc component, a glucosamine component, or a lipoic acid component may be present in the composition with hydrolyzed collagen in an amount of from about 0.1% by weight to about 50% by weight of the total composition. As another example, the composition may include a zinc component, a glucosamine component, and a lipoic acid component together in an amount of from about 0.1% by weight to about 50% by weight. The present composition (e.g., in gel form) may, for example, include from about 60% by weight to about 65% by weight hydrolyzed collagen, from about 25% by weight to about 35% by weight zinc gluconate, and from about 1% by weight to about 5% by weight sodium hyaluronate. Other amounts below and above these ranges may be used.

The composition may be prepared by mixing the ingredients described above using standard methods for achieving uniformity and dispersion. The composition may take the physical form used in topical administration selected from the group consisting of gel, solution, spray, powder, paste, foam, film, or for incorporation in a dressing bandage or a topically applied patch. The composition may be incorporated in a delivery system/membrane for controlled release of the composition. The composition may be incorporated in a petrolatum or mineral oil base.

The powder form will preferably have a moisture content of approximately 2-10 wt. % and a pH range of 5.5 to 6.5. The powder composition will have an ash content of less than 2.5 wt. % and an isotonic point of 5.0 to 6.5. In use, the powder composition may be the preferred physical form for use with irregularly shaped wounds. Tunnel wounds, flaps, and other non-conformative sites may be managed with the powder composition because it easily conforms to any shape wound, and may be applied by a poofer bottle or otherwise blown into difficult to reach wound sites. The powder is especially useful in wounds with a large amount of exudate, as the powder can absorb nearly 30 times its own weight. As the powder absorbs the exudate, a gel is formed which completely fills the wound site, forming a mechanical barrier against bacterial infection. The powder does not exhibit the characteristic fly-away when being applied to the wound site, and administration is perfected due to the precise powder placement.

The gel form of the composition is especially useful in wounds with lesser amounts of exudate, burns, and surgical sites. Application of the gel can be dispensed through a tube, syringe or the reservoir in the topical patch. The gel may be formed by adding sterile water to the powder. The gel has the added advantage of adding moisture to the wound site and stays positioned where applied. Inactive carriers of the gel form may be, for example, mineral oil, petrolatum, and water and/or water based emulsions. The composition may also be incorporated in a sodium hyaluronate gel.

A film form of the medicament composition may be made by mixing, under heat at 155-175.degree. F., the powdered form with deionized water. Cross-linking and other agents such as humectant, propylene glycol, sorbitol, and glycerine may be added to the mixture. A preservative such as benzyl alcohol or paraben can be added. The mixture is cast on a belt liner by knife on a roll coating machine to form a liquid film which is oven-dried. The film form can also be formed by a cooling the liquid solution. These films can be used for drug or other chemical delivery, and especially in dental applications. Antimicrobial and other medicinal agents can also be added to the film as needed for specific applications.

It is to be understood that the present invention is not limited to the embodiments described above, but encompasses any and all embodiments within the scope of the following claims.

I claim:

1. A method for inhibiting scar formation of wounds comprising the step of administering a composition to a site of tissue injury, the composition including about 60% by weight to about 65% by weight hydrolyzed collagen, about 25% by weight to about 35% by weight of zinc gluconate, and about 1% by weight to about 5% by weight sodium hyaluronate, wherein the hydrolyzed collagen has a molecular weight between 10,000 Daltons to about 150,000 Daltons.

2. A composition for reduced scar formation of wounds, comprising:
    about 60% by weight to about 65% by weight hydrolyzed collagen;
    about 25% by weight to about 35% by weight of zinc gluconate; and
    from about 1% by weight to about 5% by weight sodium hyaluronate,
wherein the hydrolyzed collagen has a molecular weight between 10,000 Daltons to about 150,000 Daltons.

* * * * *